(12) United States Patent (10) Patent No.: US 6,709,411 B1
Olinger (45) Date of Patent: *Mar. 23, 2004

(54) SHOULDER BRACE, AND METHODS OF USE

(76) Inventor: David R. Olinger, 1529 W. Grand Ave., Suite B, San Marcos, CA (US) 92069

( * ) Notice: Subject to any disclaimer, the term of this patent is extended or adjusted under 35 U.S.C. 154(b) by 0 days.

This patent is subject to a terminal disclaimer.

(21) Appl. No.: 09/271,827

(22) Filed: Mar. 18, 1999

(51) Int. Cl.[7] .................................................. A61F 5/00
(52) U.S. Cl. ................................................ 602/4; 602/19
(58) Field of Search ........................... 602/4, 5, 20, 21, 602/26, 62, 63; 128/845, 846, 869–876; 2/216, 305, 311, 312

(56) References Cited

U.S. PATENT DOCUMENTS

| 114,615 | A | * | 5/1871 | Smitley | 602/4 |
| 4,446,858 | A | * | 5/1984 | Verter | 602/4 |
| 4,480,637 | A | * | 11/1984 | Florek | 602/4 |
| 4,598,703 | A | * | 7/1986 | Lindemann | 602/4 |
| 5,203,763 | A | * | 4/1993 | Lajiness-O'Neill | 602/4 |

* cited by examiner

Primary Examiner—Michael A. Brown
(74) Attorney, Agent, or Firm—Thomas Fitting

(57) ABSTRACT

The invention describes a shoulder support for rehabilitation of musculo-skeletal shoulder disorders.

14 Claims, 9 Drawing Sheets

SHOULDER BRACE, AND METHODS OF USE

TECHNICAL FIELD

This invention relates to appliances used for the prevention or rehabilitation of musculo-skeletal shoulder disorders, and more particularly describes a shoulder brace.

BACKGROUND OF THE INVENTION

Shoulder dislocations, i.e., separation of the head of the humerus from the glenoid fossa, involve injury to the various soft tissues and the connective tissues usually supporting these components. Healing of such dislocations requires immobilization of the components, and for proper long-term healing, adequate support and possible range of motion limitations may be required to permit proper tissue repair and reconstruction.

Various devices and appliances have been described previously which attempt to solve the problem of providing support while at the same time permitting restricted movement to promote healing.

Coleman, U.S. Pat. No. 4,644,939, describes a device which guides the humerus upward along a longitudinal axis, but which also restricts elevation of the humerus beyond horizontal and opposes both anterior and posterior rotation.

Various other devices are described in U.S. Pat. Nos. 3,906,944, 3,499,441, 4,302,849, and 4,862,878. Although these various devices are directed at providing shoulder support, they do not allow support during the full range of motions possible for the shoulder. Instead, these devices either (1) restrict certain movements to a "safe zone" of movement, or (2) provide support (e.g., stabilizing force) in certain positions and incomplete support during other ranges of motion.

Harding et al., *J. Musculoskeletal Med.*, June:54–58 (1997) describes the limitations of known shoulder support devices for treating anterior shoulder stability. In particular, there remains to be designed a brace which maintains stability of the joint between the humerus and glenoid fossa ("gleno-humeral joint" stability) throughout the range of motions in order to allow healing during adequate functioning of the joint. In other words, it is desirable to provide gleno-humeral joint stability while allowing full range of motion and preventing hyper mobility or hyper extensions during normal movement.

Braces which limit or restrict full range of motion (ROM) do not allow proper healing throughout those restricted ranges. In contrast, braces which allow motion fail to provide joint stability, particularly anterior instability during abduction, external rotation and extension movements.

BRIEF SUMMARY OF THE INVENTION

A device has now been discovered that provides full range of motion at the same time that gleno-humeral joint stability is maintained, including abduction, external rotation and extension.

DETAILED DESCRIPTION OF THE INVENTION

A. Definitions

"Abduction" refers to the motion in the shoulder joint as an straight extended arm is moved from pointing forward to pointing sideways.

"Anterior" refers to the direction forward and perpendicular to the head to toe axis and perpendicular to the right to left axis, and is the opposite of "posterior".

"Anterior instability" refers to excessive anterior translation of the humeral head in the glenoid fossa.

"Extension" refers to the motion in the shoulder joint as the elbow is moved in an arc from adjacent to the side of the trunk to pointing sideways.

"External rotation" refers to the motion in the shoulder joint as the hand is moved in an arc from adjacent to the stomach to pointing sideways while keeping the elbow positioned adjacent to the side of the trunk, and is the opposite of "internal rotation".

"Superior" refers to the direction upwards and towards the head end on the head to toe axis, and is the opposite of "inferior".

B. Shoulder Brace Structure

The present invention describes a shoulder stabilization and joint compression device having two basic features: a trunk engaging means (1) and the shoulder joint compression and stabilization means.

Figure 2:
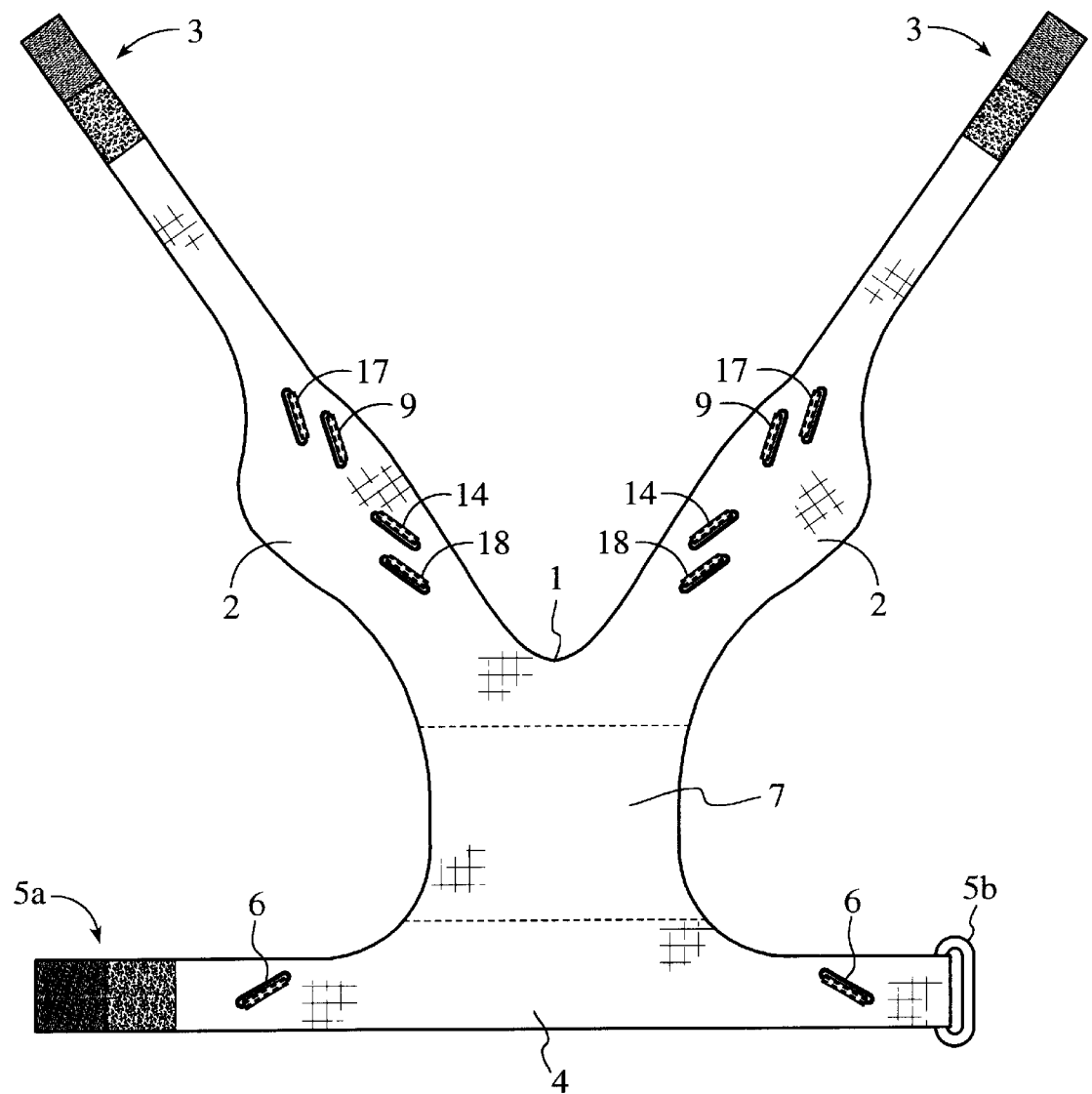
FIG. 2 is a dorsal view of the trunk engaging means of the shoulder brace in an open position, i.e., without any of the fasteners or engaging means connected.

The trunk engaging means (1), as seen in FIG. 2, comprises two shoulder straps referred to as the left and right shoulder support means (2), an abdomen belt (4) comprised of left and right abdomen engaging means and a back panel midsection (7) which connects the shoulder support means to the abdomen belt on the dorsal side of the trunk. The trunk engaging means is held in place on the wearer's body by virtue of adjustable attachment means on both the shoulder straps and on the abdomen belt.

The ends of the left and right shoulder support means have engaging means (3) which are adapted to attach (engage) to the abdomen belt at right and left shoulder support anchor means (6) positioned respectively on the belt about midway between the medial and dorsal center lines of the belt such that the shoulder support straps (2) criss-cross the chest.

The abdomen engaging means (4) includes complementary left and right fasteners (5A and 5B) which allow adjustable closure of the abdomen belt around the abdomen region of the trunk.

The shoulder joint compression and stabilization means comprises an upper arm cuff (10) that encloses the upper arm, and lift assist means (8) which connect at their superior ends to anterior (9) and posterior (14) anchor means on the shoulder support means (2) and which connect at their inferior ends to anchor means (11) on the upper arm cuff. The lift assist means criss-cross over the superior lateral region of the upper arm such that the anterior lift assist on the ventral side crosses and attaches to the anchor means on the posterior side of the cuff and the posterior lift assist on the dorsal side crosses and attaches to the anchor means on the anterior side of the cuff.

Figure 1:
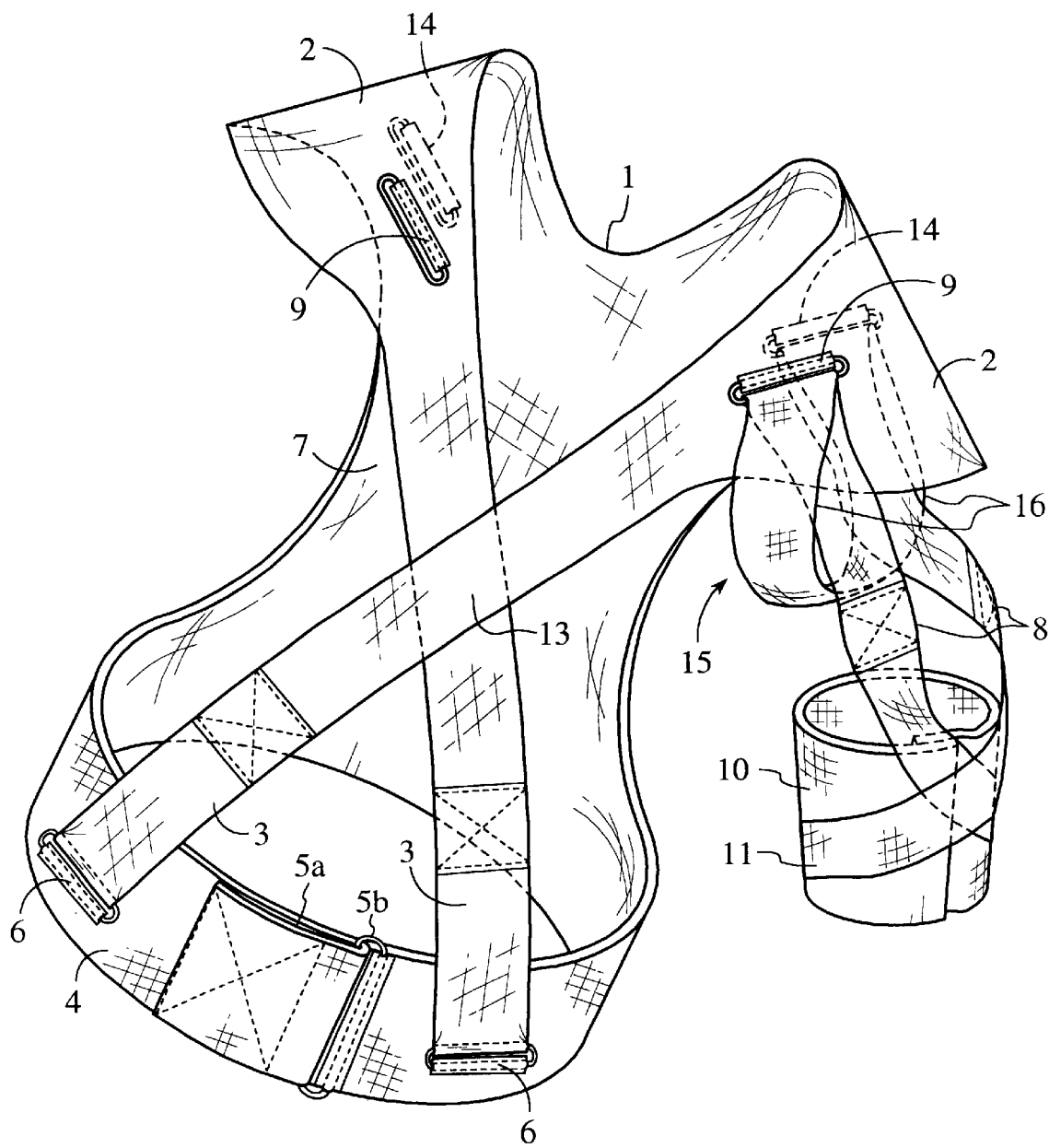
FIG. 1 is an anterior view of the shoulder brace without a human body, with the straps displayed in the closed (attached) position as if being worn to illustrate the complete shape of the brace.
Figure 9:
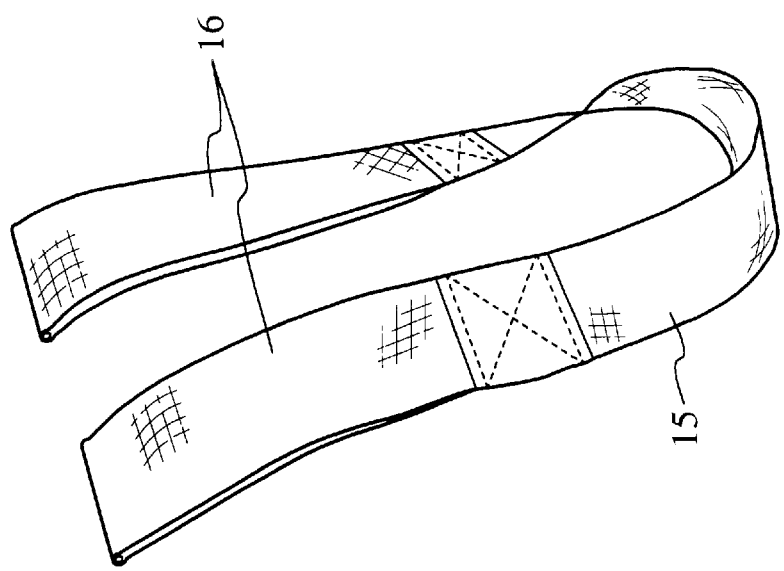
FIG. 9 is a detailed view of the under arm engaging means.
Figure 10:
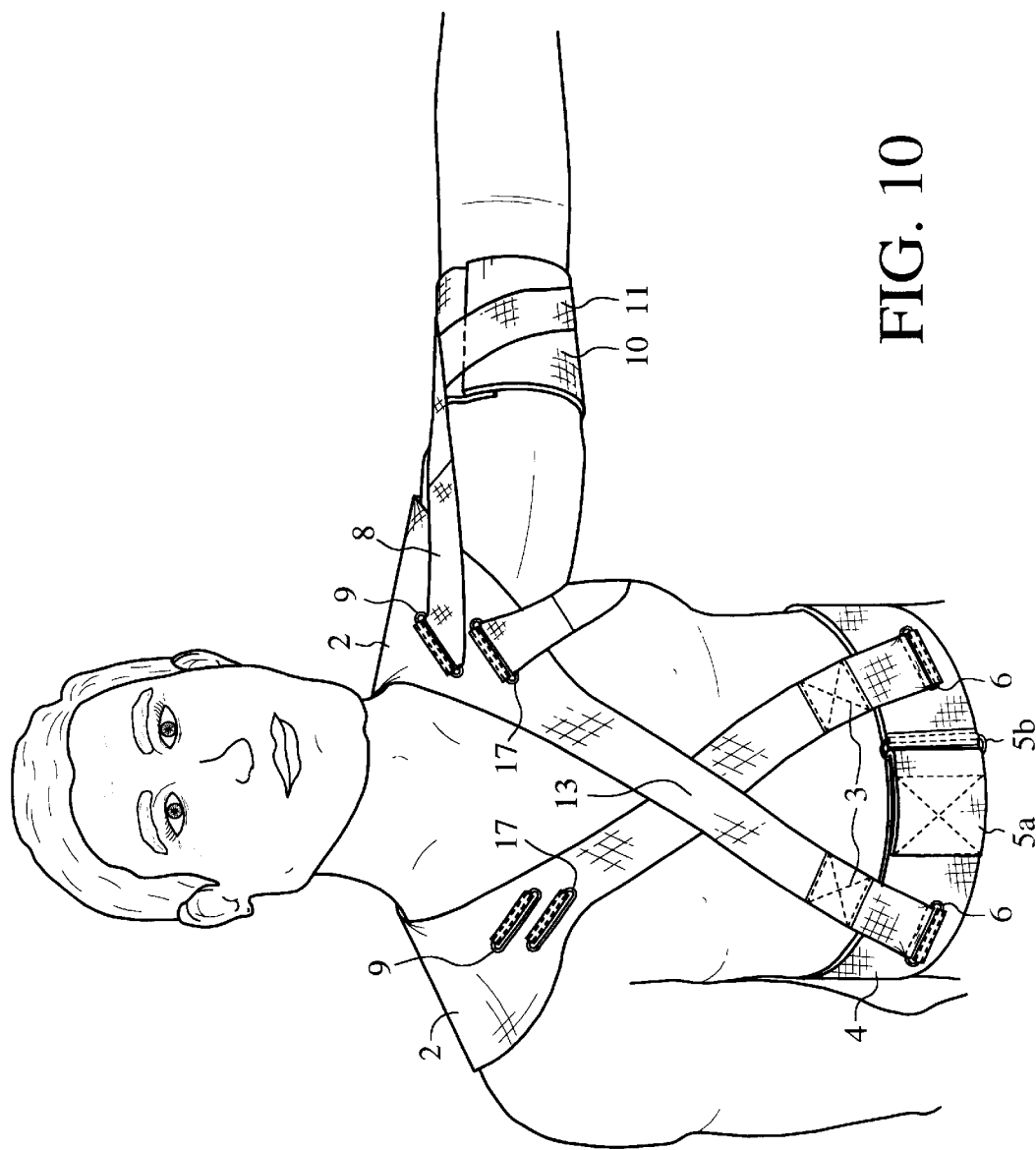
FIG. 10 is an anterior view of the shoulder brace that includes the under arm engaging means and is worn by a man with the left arm fully extended.

In some situations, it is desirable to provide a superior force to maintain vertical stability of the shoulder joint and restrict inferior, anterior and/or posterior shoulder joint dislocations. The optional under arm engaging means (15) is shown in FIG. 1, in FIG. 6 and in FIG. 9 with the anterior and posterior engaging means (16) attached to the shoulder support means at the respective anterior (9) and posterior (14) anchor means. The under arm engaging means (16) can optionally connect onto anterior (17) and posterior (18) anchor means positioned separate from anchor means (9) and (14) as shown in FIG. 10.

C. Operation of the Shoulder Brace

The present brace provides a combination of glenohumeral joint compression and stability throughout a full range of motions. These aspects are provided by virtue of several design aspects of the present shoulder brace.

Figure 7:
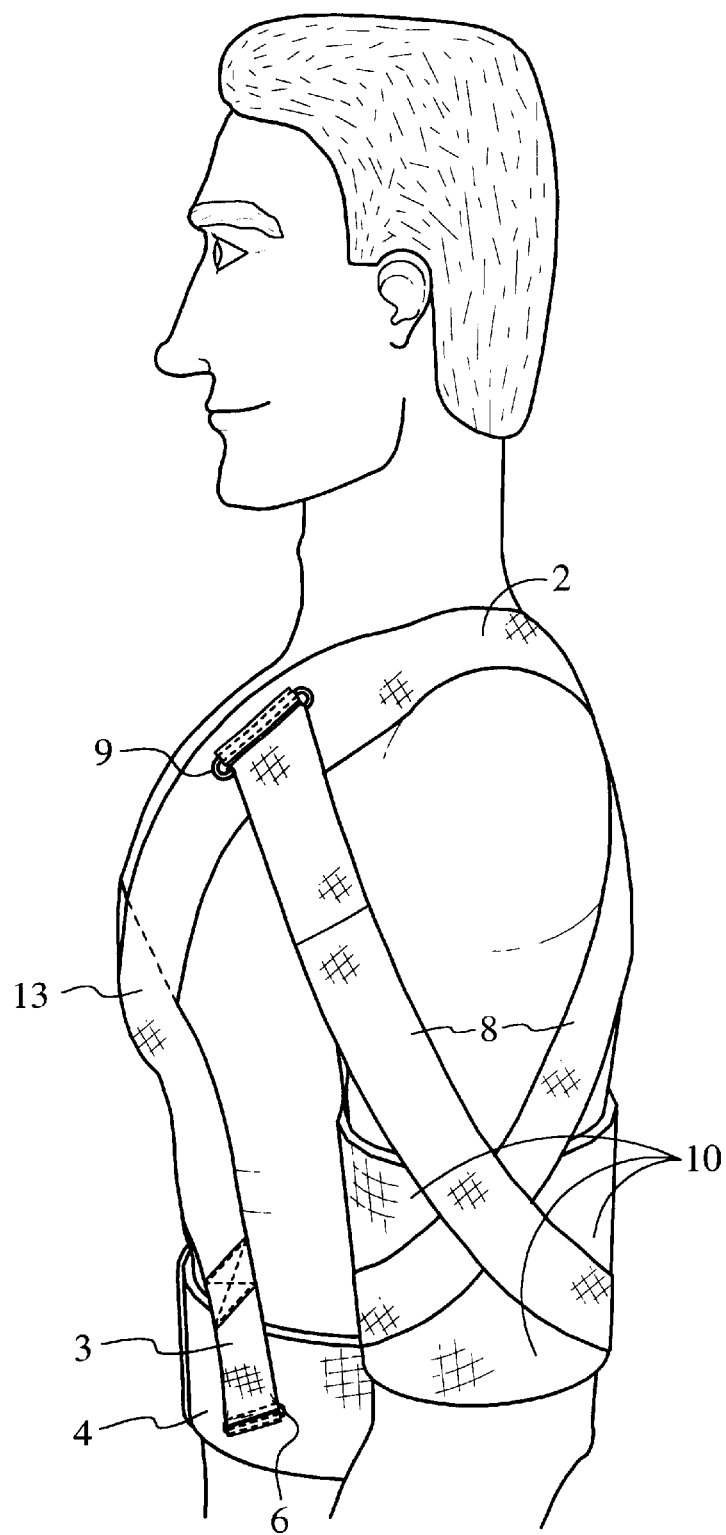
FIG. 7 is a medial (side) view of the brace worn by a man showing the arm with the shoulder stabilization means.
Figure 8:
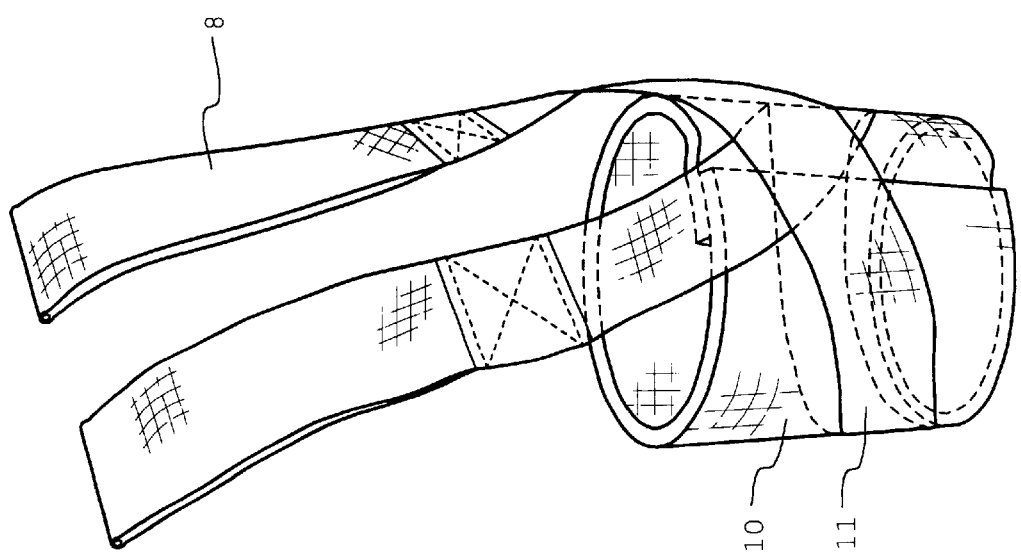
FIG. 8 is a detailed view of the shoulder stabilization means, with arm cuff and lift assist means.

The criss-cross feature of the lift assist means (8), illustrated in FIG. 7 and FIG. 8, provides support throughout the range of motion including abduction, extension and external rotation. The lift assist means are positioned to provide a superior medial compression of the humeral head into the glenoid fossa throughout a range of motions. This compression occurs by the combined and independent forces of the superior and anterior lift assist means, which forces are redirected onto the joint in a supportive direction as the arm is manipulated throughout a full range of motion. Importantly, the tension of the anterior and posterior lift assist means can be independently adjusted such that the "resting" state of the brace provides stability for either an anterior or posterior instability, by exerting a combination of forces that is resting in either an internal or external rotation position.

The criss-cross feature of the lift assist means around the arm also insures that the respective forces that stabilize anterior and posterior translations cooperate as the shoulder joint is externally or internally rotated.

Figure 3:
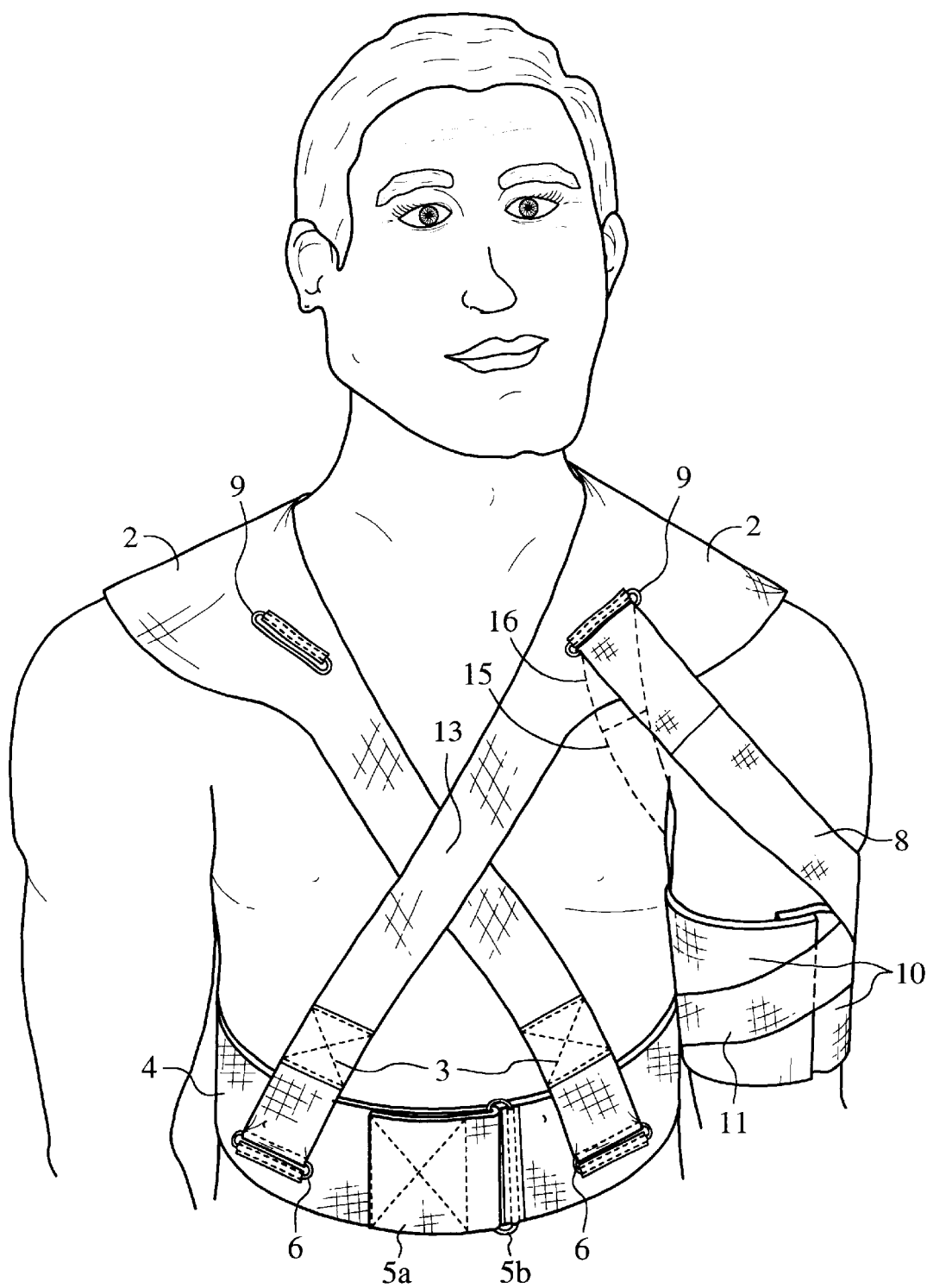
FIG. 3 is an anterior view of the shoulder brace worn by a man.
Figure 4:
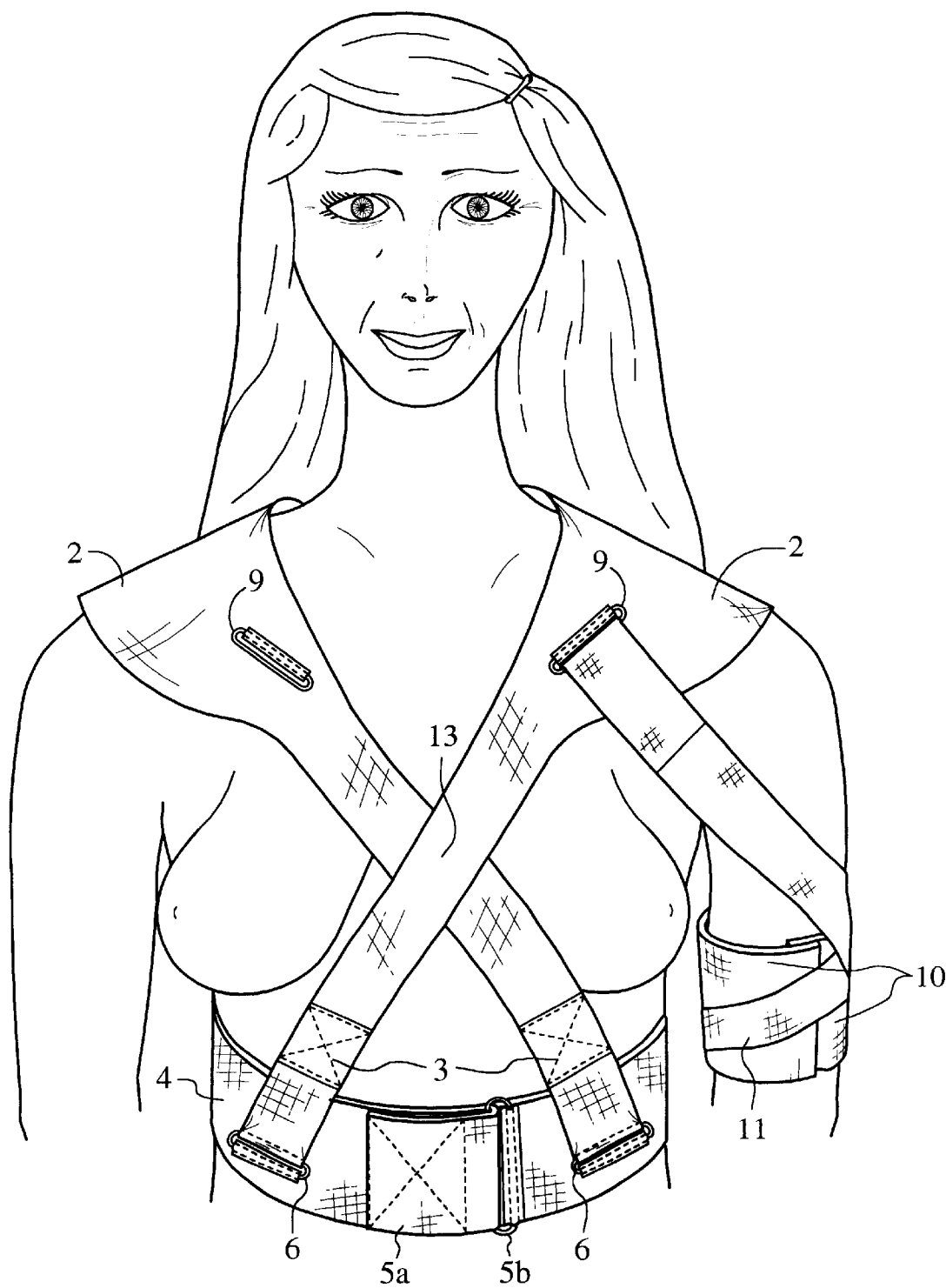
FIG. 4 is an anterior view of the shoulder brace worn by a woman.
Figure 5:
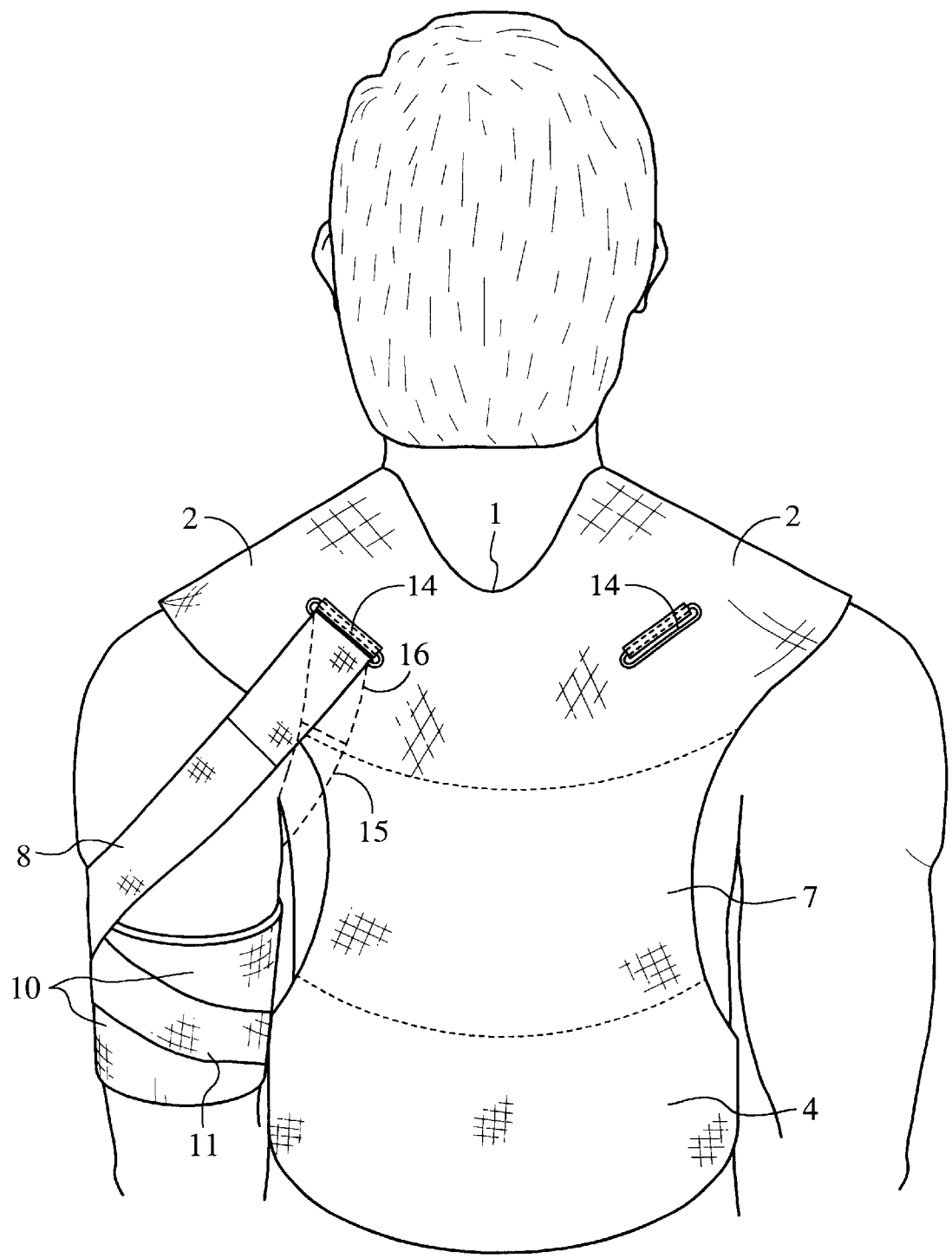
FIG. 5 is a dorsal view of the shoulder brace worn by a man.
Figure 6:
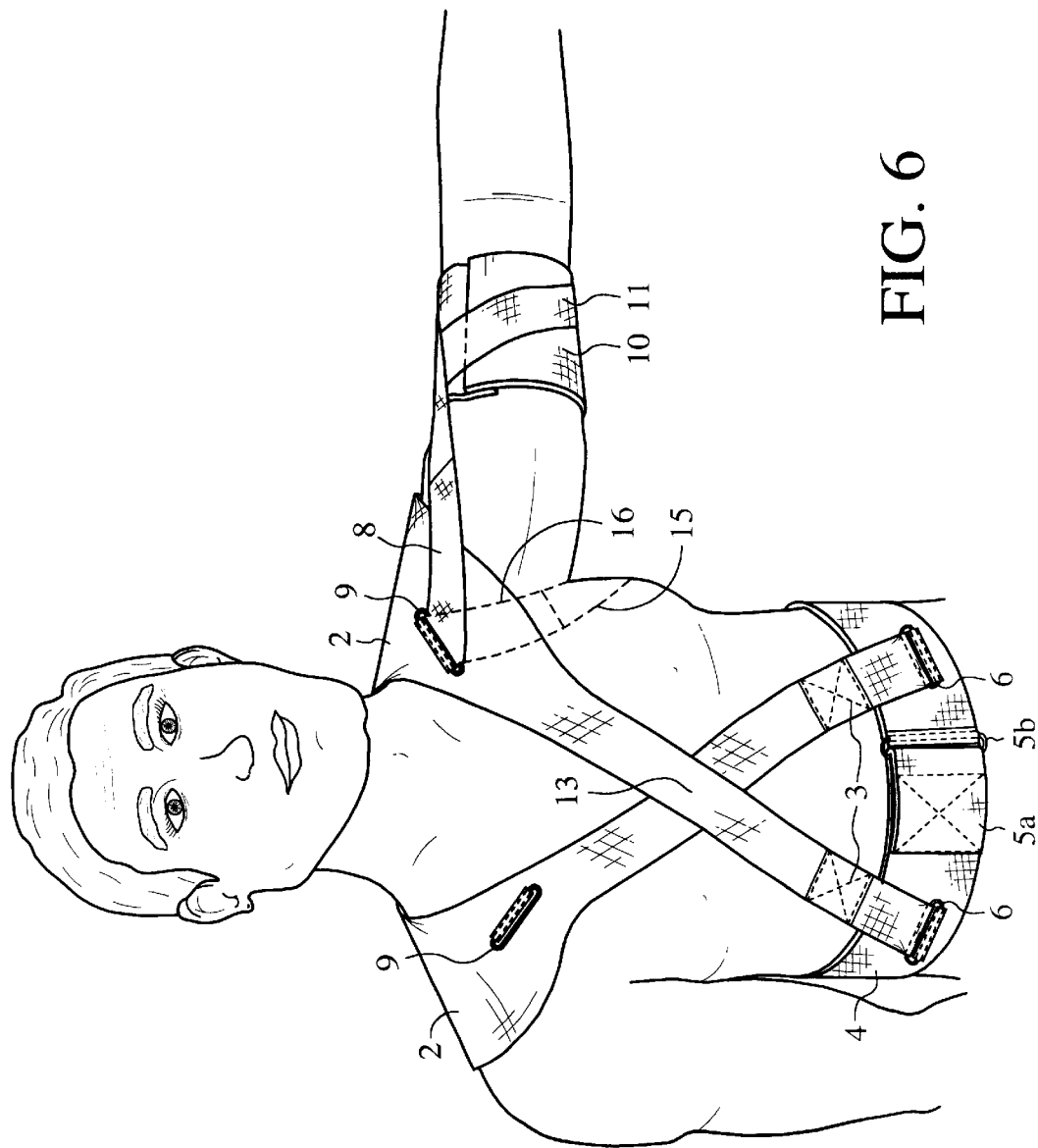
FIG. 6 is an anterior view of the shoulder brace worn by a man with the left arm fully extended.

In addition, as seen by comparing FIG. 3 and FIG. 6, the position of the lift assist means primarily favors a superior medial compression until the arm is fully extended, at which point the compression is not superior against the acromioclavicular joint. Compression of the humerus against the acromium process is limited in the extended position.

Also shown by comparing FIG. 3 and FIG. 6, the use of the optional under arm engaging means restricts inferior displacements, particularly when the arm is extended.

The brace restricts hyper mobility by providing some degree of stabilization through the opposing forces of the criss-cross lift assist means. However, due to the position of the lift assist means and its elastic character, the range of motion restrictions are minimal as compared to an inelastic panel or strap, and the present brace allows all normal range of motion movements with force-motivated rotations, abductions and extensions. The result is that shoulder movements, although permitted, are assisted and thereby controlled, including controlled shoulder rotations, scapulothoracic motions and arm extensions.

The upper arm cuff is designed to hold the arm for purposes of supporting the humeral head into the glenoid fossa, and is typically able to enclose the inferior portion of the upper arm. For comfort, it is undesirable to cover more of the arm than is necessary, and therefore is seen that a strap or cuff in cylinder length of from about one-half to one-fifth, and preferably about one-third to one-quarter, of the length of the humerus is suitable. The cuff can be an elastic cylindrical cone tapered to fit the arm, or it can be a strap with a fastener for wrapping about the arm. The strap design is shown in FIG. 8, where the ends of the strap are connected, typically by Velcro.

The upper arm cuff can have a variety of anchor means for securing the lift assist means at their inferior ends to the cuff. A preferred anchor means is a large section of Velcro around the circumference of the cuff to accommodate changes in the angle and extent of criss-cross wrap by the lift assist means, which contains a complementary engaging means on the inferior ends.

The point of attachment for the lift assist means onto the shoulder support means at the anterior and superior anchor means is important for providing the appropriate angle of lift assist for compression and stability of the joint. The anterior anchor means is preferably located just inferior to the midline of the clavicle, positioned preferably within one inch of the clavicle. The posterior anchor means is preferably located just superior to the midline of the scapular spine, positioned preferably within one inch of the spine.

The criss-cross feature (13) of the shoulder support means also provides important advantages to the present shoulder brace. A primary purpose is to provide support for the anterior and posterior lift assist means at a point and angle critical for proper support of the arm and shoulder. The criss-cross feature provides a support for the lift assist means that is angled rather than vertical. A vertical support is inferior to the present design because the anchor means for the lift assist cannot easily be pulled axially outward by virtue of its own angled anchor on the abdomen belt on the opposite side of the trunk, and therefore provides firm support for the lift assist to attach. In the angled support of the criss-cross, the brace maintains an angle of support for the lift assist means throughout the full range of motion.

The criss cross feature (13) also provides a unique design feature that allows the brace to be used by both men and women without modification. In particular, the design of the brace and the shoulder support means as support for the lift assist means allows the brace to be worn by an adult woman appropriately engaging the trunk in a functional manner without interfering with the breasts and without the breasts interfering with the brace as it engages the trunk.

D. Construction of the Shoulder Brace

The shoulder brace of this invention can be constructed using a variety of materials, and by a variety of manufacturing methods.

The lift assist means and the left and right shoulder support means are constructed of any of a variety of materials which provide elastic support, and can include any material manufactured or woven to provide a directional elasticity in the direction of the lift assist means from superior to inferior ends. These materials can include any two-way orthopedic stretch fabric including but not limited to rubberized cloths and straps, synthetic polymer meshes such as Lycra and Spandex, elastic plastic materials, neoprene, vinyl, latex, and the like.

The trunk engaging means can be constructed from any of a variety of material, which can include elastic or inelastic fabrics or other materials, including the above mentioned elastic materials for the lift assist means. Inelastic materials can include canvas, cloth, polymer mesh and the like materials. For comfort and because of the discomforts associated with perspiration, it is preferred that the materials be porous to air and moisture whenever possible, such as by the use of open mesh materials on the back panel midsection.

Anchor and attachment means are used at various parts of the invention, including the abdomen engaging means complementary fasteners (5A and 5B), the shoulder support engaging means (3) attached to the shoulder support anchor means (6), and the lift assist means where the superior ends attach to the anterior (9) and posterior (14) anchor means and the inferior ends attach by engaging means onto the upper arm cuff anchor means. These connections can be made by any of a variety of attachment devices, both removable and permanent, and therefore the invention need not be so limited. The specific examples given herein are intended as illustrative only, and include buckles, slip-lock buckles, snaps, button and eye fasteners, eye and hook fasteners, Velcro, and the like removable attachment means. Where a fixed attachment is desired that is not readily detachable, a more permanent method can be used, included by stitch, staple, brad, screw, adhesive, and the like permanent attachment means. Particularly preferred is Velcro because of the flexibility in tension adjustment and because it accommodates adjustment made where only one hand is available.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A shoulder support for rehabilitation or treatment of musculo-skeletal shoulder disorders comprising:
   a) a trunk engaging means (1) comprising
      i) left and right shoulder support means (2) including left and right shoulder support engaging means (3);
      ii) left and right abdomen engaging means (4) including complementary left and right fasteners (5A, 5B) and left and right shoulder support anchor means (6); and
      iii) a back panel midsection (7) connecting said shoulder support means to said abdomen engaging means, wherein said left and right abdomen engaging means form a sub-thoracic abdominal trunk enclosing strap when said left and right abdomen engaging means are engaged;
      and wherein said left and right shoulder support means cross over the chest and attach by said shoulder support engaging means to said respective right and left shoulder support anchor means, thereby engaging said trunk; and
   b) shoulder joint compression and stabilization means comprising
      i) anterior and posterior lift assist means (8) having superior and inferior ends;
      ii) anterior (9) and posterior (14) anchor means on said shoulder support means for attaching said superior ends of said lift assist means to said shoulder support means;
      iii) an upper arm cuff (10) enclosing the inferior portion of the upper arm and comprising cuff anchor means (11) for attaching said inferior ends of said lift assist means to said cuff; and
      iv) engaging means on said inferior ends of each of said lift assist means capable of engaging said cuff anchor means (11);
         wherein said anterior and posterior lift assist means criss-cross over the superior lateral region of the upper arm and attach to said cuff anchor means;
         whereby said shoulder brace compresses the shoulder joint and stabilizes the joint without restricting full range of motion of the arm.

2. The support of claim 1 wherein said trunk engaging means is adjustable as to position and tension at each of said left and right shoulder support engaging means and said left and right abdomen engaging means.

3. The support of claim 1 wherein said upper arm cuff comprises a flexible material in the shape of a cylinder which can be slid over the hand and onto said inferior portion of the upper arm.

4. The support of claim 1 wherein said upper arm cuff comprises a flexible material in the shape of a strap which can be wrapped around said inferior portion of the upper arm, thereby enclosing said inferior portion.

5. The support of claim 1 wherein said engaging means on said inferior ends of said lift assist means are permanently attached to said cuff anchor means.

6. The support of claim 1 wherein said engaging means on said inferior ends of said lift assist means are removably attachable to said cuff anchor means.

7. The support of claim 6 wherein said removably attachable engaging means comprise a buckle, snap or hook and loop or hook and pile fastener.

8. The support of claim 1 wherein said left and right shoulder support means comprise an elastic material to provide trunk engagement throughout a complete range of trunk, arm and shoulder motions.

9. The support of claim 8 wherein said elastic material is selected from the group consisting of neoprene, rubber, latex and woven fabric.

10. The support of claim 1 wherein said anterior and posterior lift assist means comprise an elastic material to provide elastic lift to said cuff and thereby compressing the shoulder joint throughout a complete range of arm and shoulder motions.

11. The support of claim 10 wherein said elastic material is selected from the group consisting of neoprene, rubber, latex and woven fabric.

12. The support of claim 1 wherein said left and right shoulder support means comprise a narrow strap section (13) in the region where said support means cross over the chest to accommodate a female anatomy by not substantially engaging the breasts while engaging said trunk.

13. The support of claim 1 which further comprises an under arm engaging means (15) comprising anterior and posterior engaging means (16) for attaching said under arm engaging means to said respective anterior and posterior anchor means on said shoulder support means, whereby said under arm engaging means restricts inferior, anterior or posterior shoulder joint dislocations.

14. The support of claim 13 wherein said anchor means for said under arm engaging means are removable at one or both of said anterior or posterior anchor means.

* * * * *